United States Patent
Hopper et al.

(10) Patent No.: US 8,303,484 B2
(45) Date of Patent: Nov. 6, 2012

(54) SELF-PROPELLED ROBOTIC DEVICE THAT MOVES THROUGH BODILY AND OTHER PASSAGEWAYS

(75) Inventors: Peter J. Hopper, San Jose, CA (US); Philipp Lindorfer, San Jose, CA (US); William French, San Jose, CA (US); Visvamohan Yegnashankaran, Cupertino, CA (US)

(73) Assignee: National Semiconductor Corporation, Santa Clara, CA (US)

( * ) Notice: Subject to any disclaimer, the term of this patent is extended or adjusted under 35 U.S.C. 154(b) by 516 days.

(21) Appl. No.: 12/621,719

(22) Filed: Nov. 19, 2009

(65) Prior Publication Data
US 2011/0118607 A1    May 19, 2011

(51) Int. Cl.
*A61B 1/00* (2006.01)
(52) U.S. Cl. ......................... 600/115; 600/116
(58) Field of Classification Search .......... 600/114–116, 600/466
See application file for complete search history.

(56) References Cited

U.S. PATENT DOCUMENTS

| | | | | |
|---|---|---|---|---|
| 5,651,366 | A * | 7/1997 | Liang et al. | 600/439 |
| 6,764,441 | B2 | 7/2004 | Chiel et al. | |
| 6,833,767 | B1 * | 12/2004 | Huff et al. | 331/17 |
| 6,988,986 | B2 * | 1/2006 | Gross | 600/114 |
| 7,172,552 | B2 | 2/2007 | Wendlandt | |
| 7,181,267 | B2 | 2/2007 | Barbato | |
| 7,329,223 | B1 | 2/2008 | Ainsworth et al. | |
| 7,426,409 | B2 | 9/2008 | Casscells, III et al. | |
| 7,534,204 | B2 | 5/2009 | Starksen et al. | |
| 7,567,843 | B2 | 7/2009 | Eggers et al. | |
| 2003/0065250 | A1 * | 4/2003 | Chiel et al. | 600/115 |
| 2006/0064081 | A1 * | 3/2006 | Rosinko | 606/27 |
| 2008/0123383 | A1 * | 5/2008 | Shionoiri | 363/127 |

OTHER PUBLICATIONS

Zimmerman et al. "Worm-Like Locomotion. Ways of Realization: Non-Symmetric Friction and application of Ferrofluids". Technishe Universitat Ilmenau, 2007. Web Jun. 11, 2012. <http://tu.ilmeanau.de/fakmb/Worm-like-Locomotion.4075.0.html?&print=1>.*

Irwan Kassim et al, "Locomotion Techniques for Robotic Colonoscopy," IEEE Engineering in Medicine and Biology Magazine, May/Jun. 2006, pp. 49-56.

Paolo Dario et al, "Smart Surgical Tools and Augmenting Devices," IEEE Transactions on Robotics and Automation, vol. 19, No. 5, Oct. 2003, pp. 782-792.

* cited by examiner

*Primary Examiner* — Clayton E Laballe
*Assistant Examiner* — Minh Phan
(74) *Attorney, Agent, or Firm* — Eugene C. Conser; Wade J. Brady, III; Frederick J. Telecky, Jr.

(57) ABSTRACT

A self-propelled robotic device moves through bodily and other passageways by inflating regions of an overlying bladder along the length of the robotic device in a sequence that imparts motion to the device. The regions of the overlying bladder are inflated by energizing a plurality of coils, which are surrounded by a ferrofluid, in a sequence. The ferrofluid responds to the magnetic field created by an energized coil by creating a bulge in the side wall of the overlying bladder.

14 Claims, 14 Drawing Sheets

SELF-PROPELLED ROBOTIC DEVICE THAT MOVES THROUGH BODILY AND OTHER PASSAGEWAYS

BACKGROUND OF THE INVENTION

1. Field of the Invention

The present invention relates to robotic devices and, more particularly, to a self-propelled robotic device that moves through bodily and other passageways.

2. Description of the Related Art

A significant advance in the performance of surgical procedures is the development of minimally invasive surgery. With minimally invasive surgery, a long tubular device, such as an endoscope, a catheter, or a colonoscope, is inserted into a bodily passageway, such as an artery, a vein, or a colon, by way of a minor incision or a natural opening in the body.

Once inside the body, the device is pushed through the bodily passageway by a surgeon to evaluate the condition of the passageway and/or the condition of an organ, such as the heart, that can be accessed by way of the bodily passageway. When necessary, the device is used to perform a surgical procedure.

Minimally invasive surgery has the advantage of greatly reducing the recovery time for the patient. In the case of an evaluation, the only impact to the body is that required to gain access to the bodily passageway. Further, in the case of a surgical procedure, the impact to the body is limited to the bodily passageway and/or organ where the surgery is performed (along with any incision that is necessary to access the bodily passageway).

One of the limitations of minimally invasive surgery, particularly with a colonoscope, is that it is often difficult to guide the instrument. For example, it is difficult to push a colonoscope around the many right angle bends in the colon. Thus, there is a need for a self-propelled robotic device that can move through bodily and other passageways.

BRIEF DESCRIPTION OF THE DRAWINGS

FIG. 9A is a cross-sectional view taken along line 9-9 of FIG. 1 in accordance with a first embodiment, while FIG. 9B is a cross-sectional view taken along line 9-9 of FIG. 1 in accordance with a second embodiment.

FIG. 10A is a longitudinal cross-sectional view of the back steering coil section of central tube 110, while FIG. 10B is a cross-sectional view taken along line 10B-10B of FIG. 10A.

FIG. 12A is a cross-sectional view taken along line 12-12 of FIG. 1 when treatment coil TC is de-energized, while FIG. 12B is a cross-sectional view taken along line 12-12 of FIG. 1 when treatment coil TC is energized.

DETAILED DESCRIPTION OF THE INVENTION

Figure 1:
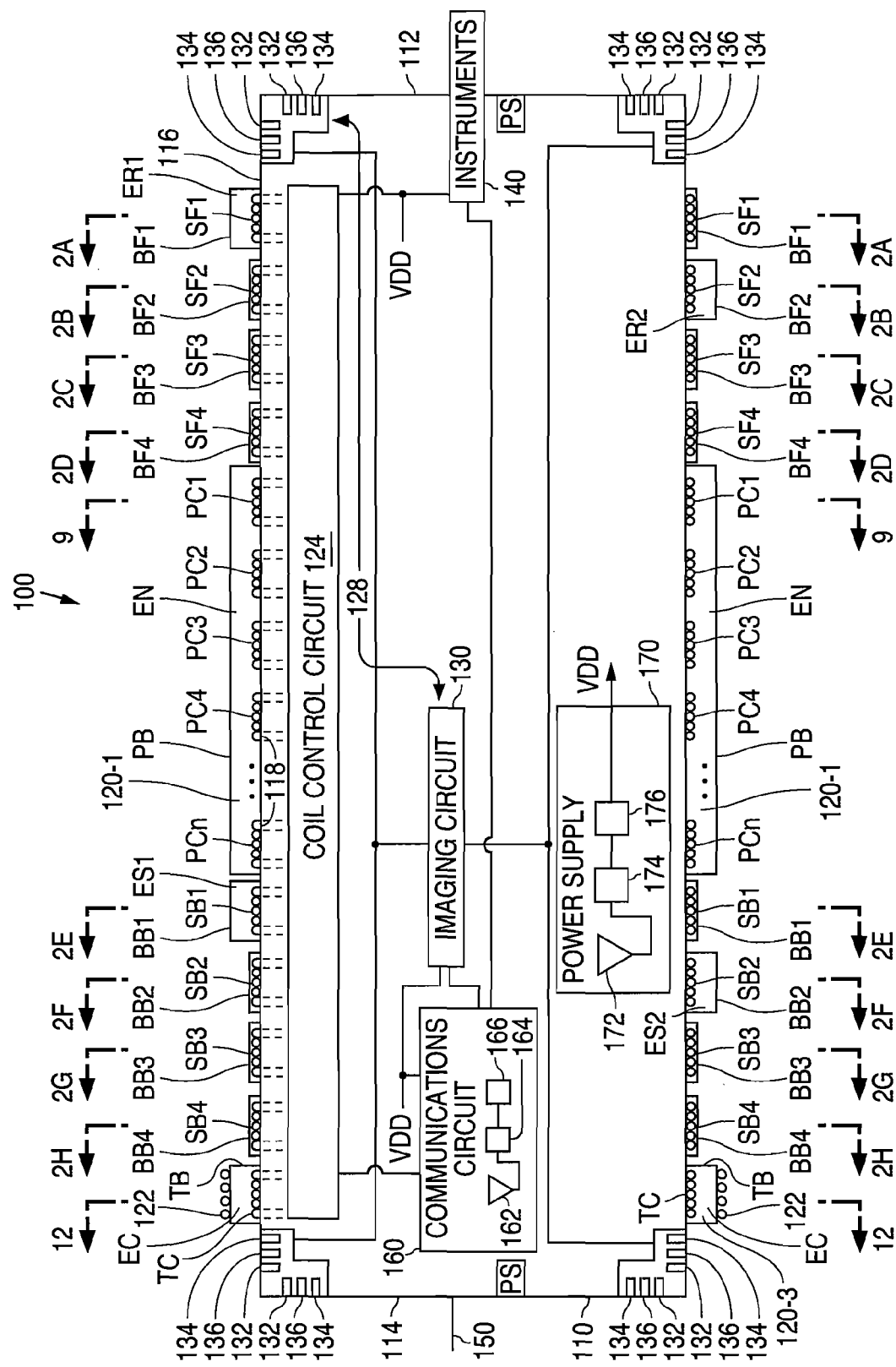
FIG. 1 is a longitudinal cross-sectional view illustrating an example of a robotic device 100 in accordance with the present invention.
Figure 2A:
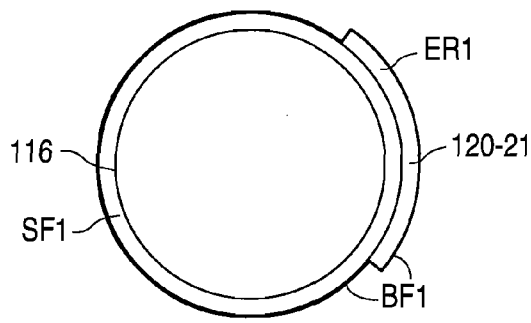
FIGS. 2A-2H are cross-sectional views taken along lines 2A-2A, 2B-2B, 2C-2C, 2D-2D, 2E-2E, 2F-2F, 2G-2G, and 2H-2H, respectively, of FIG. 1 in accordance with the present invention.
Figure 2B:
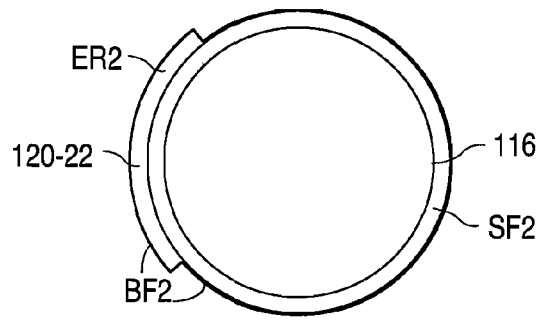
Figure 2C:
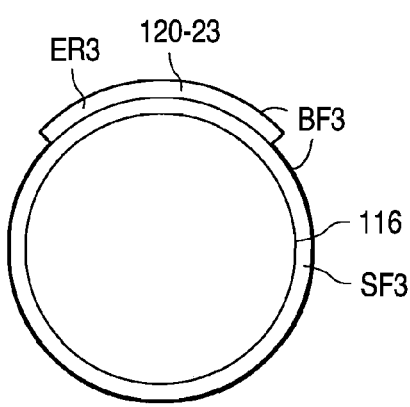
Figure 2D:
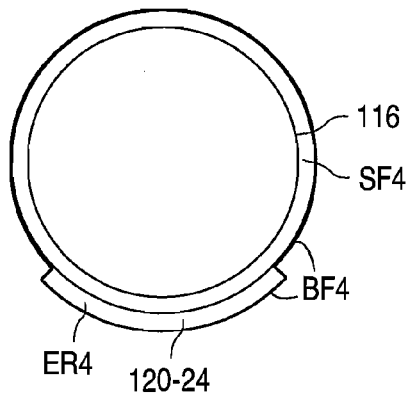
Figure 2E:
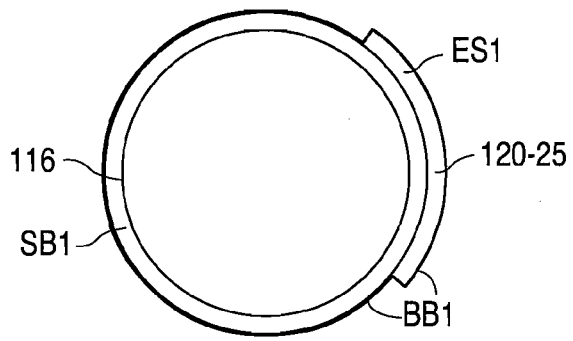
Figure 2F:
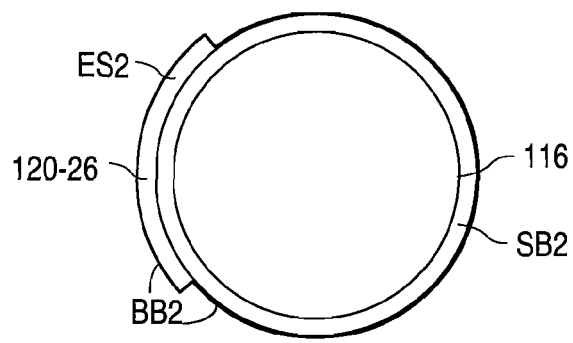
Figure 2G:
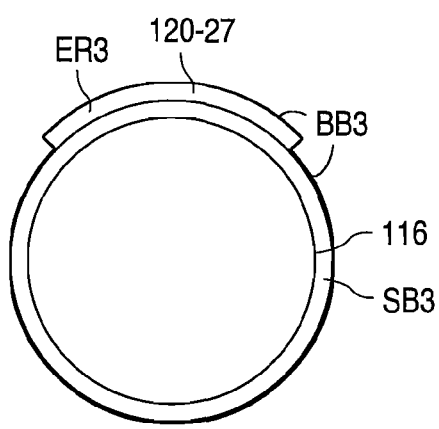
Figure 2H:
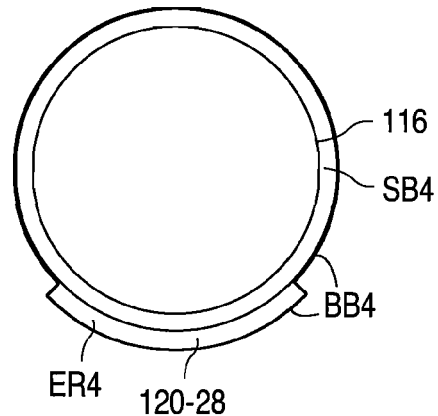

FIG. 1 shows a longitudinal cross-sectional view that illustrates an example of a robotic device 100 in accordance with the present invention. As described in greater detail below, robotic device 100 is a self-propelled device that traverses bodily and other passageways, provides a platform for imaging the interior of a passageway and/or a structure accessed by way of the passageway and, in medical applications, for delivering surgical instruments to a surgical site.

As shown in FIG. 1, robotic device 100 includes a central tube 110, a front end cap 112, and a back end cap 114. Central tube 110, which is fluid impermeable, has a longitudinal side wall 116 and a number of openings 118 that extend through longitudinal side wall 116. Front end cap 112, in turn, is attached to side wall 116 at a front longitudinal end, while back end cap 114 is attached to side wall 116 at an opposing back longitudinal end.

Central tube 110 can be implemented as a rigid or an elastic, longitudinally-compressible structure. For example, an elastic, longitudinally-compressible central tube can be implemented by attaching a tubular bladder to a coil spring. The tubular bladder, in turn, can be implemented with latex or other similar materials.

In addition, robotic device 100 includes a number of insulated wires that are wrapped around central tube 110 to form a number of coils. In the present example, the coils include a number of propulsion coils PC1-PCn, four front steering coils SF1-SF4, four back steering coils SB1-SB4, and a treatment coil TC.

Each coil can be formed with a single layer of wraps as shown in FIG. 1, or alternately with multiple layers of wraps. In addition, each coil has first and second ends that extend through the openings 118 into central tube 110. The front and back end caps 112 and 114 and the openings 118 are sealed to prevent any material from entering central tube 110.

Further, robotic device 100 includes a number of external bladders that are sealed to longitudinal sidewall 116 to cover the coils. In the present example, the external bladders include a propulsion bladder PB that is sealed to longitudinal sidewall 116 to cover the propulsion coils PC1-PCn. The sealing of the openings 118 around the portions of the propulsion coils PC that extend through central tube 110, and the sealing of propulsion bladder PB to longitudinal sidewall 116 form a propulsion fluid containment region EN that touches and lies above the propulsion coils PC1-PCn.

In the present example, the external bladders also include a number of front steering bladders BF that correspond with the number of front steering coils SF, and a number of back steering bladders BB that correspond with the number of back steering coils SB. Thus, in the present example, four front steering bladders BF1-BF4 and four back steering bladders BB1-BB4 are illustrated.

The front steering bladders BF1-BF4 are sealed to longitudinal sidewall 116 to cover the front steering coils SF1-SF4 so that each front steering bladder BF covers a corresponding front steering coil SF. Similarly, the back steering bladders BB1-BB4 are sealed to longitudinal sidewall 116 to cover the back steering coils SB1-SB4 so that each back steering bladder BB covers a corresponding back steering coil SB.

The sealing of the openings 118 around the portions of the front steering coils SF that extend through central tube 110, and the sealing of front steering bladders BF to longitudinal sidewall 116 form a corresponding number of steering fluid containment regions ER. As a result, four steering fluid containment regions ER1-ER4 are formed to touch and lie above the four front steering coils SF1-SF4 so that each steering fluid containment region ER is formed to touch and lie above a corresponding front steering coil SF.

Similarly, the sealing of the openings 118 around the portions of the back steering coils SB that extend through central tube 110, and the sealing of back steering bladders BB to longitudinal sidewall 116 form a corresponding number of steering fluid containment regions ES. As a result, four steering fluid containment regions ES1-ES4 are formed to touch and lie above the four back steering coils SB1-SB4 so that each steering fluid containment region ES is formed to touch and lie above a corresponding back steering coil SB.

In the present example, each steering bladder is permanently attached to a 270° portion of a corresponding steering coil. As a result, each steering fluid containment region ER and each steering fluid containment region ES lie above only a 90° portion of a corresponding steering coil SF and SB, respectively.

FIGS. 2A-2H show cross-sectional views taken along lines 2A-2A, 2B-2B, 2C-2C, 2D-2D, 2E-2E, 2F-2F, 2G-2G, and 2H-2H, respectively, of FIG. 1 in accordance with the present invention. As shown in FIGS. 2A-2D, the front steering bladders BF1-BF4 are permanently attached to a 270° portion of the corresponding front steering coils SF1-SF4 so that the steering fluid containment regions ER1-ER4 lie above only a 90° portion of the corresponding front steering coils SF1-SF4.

Similarly, as shown in FIGS. 2E-2H, the back steering bladders BB1-BB4 are permanently attached to a 270° portion of the corresponding back steering coils SB1-SB4 so that the steering fluid containment regions ES1-ES4 lie above only a 90° portion of the corresponding back steering coils SB1-SB4. Although the present example shows that only a 90° portion of each steering fluid containment region lies above a corresponding steering coil, a greater or lesser amount can alternately be used.

Referring back to FIG. 1, the external bladders of the present example further include a treatment bladder TB that is sealed to longitudinal sidewall 116 to cover treatment coil TC. The sealing of the openings 118 around the portions of the treatment coil TC that extend through central tube 110, and the sealing of treatment bladder TB to longitudinal sidewall 116 form a treatment fluid containment region EC that touches and lies above the treatment coil TC.

The propulsion bladder PB, the front steering bladders SF, the back steering bladders SB, and the treatment bladder TB are fluid-impermeable bladders that can be implemented with latex or other similar materials. In addition, when central tube 110 is formed as an elastic, longitudinally-compressible structure, robotic device 100 also includes a tubular mesh that touches propulsion bladder PB.

Figure 3:
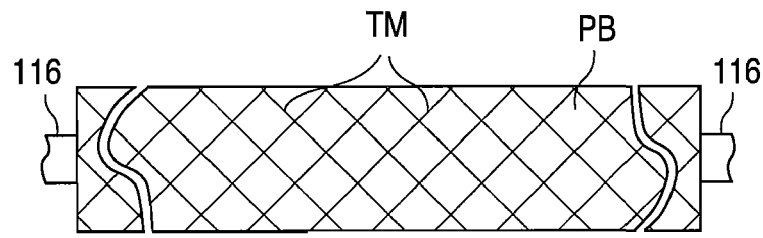
FIG. 3 is a cross-sectional view illustrating an example of a portion of robotic device 100 in accordance with the present invention.

FIG. 3 shows a cross-sectional view that illustrates an example of a portion of robotic device 100 in accordance with the present invention. As shown in FIG. 3, robotic device 100 includes a tubular mesh TM that touches and lies over propulsion bladder PB, and is attached to side wall 116 at the front and back ends of propulsion bladder PB. Tubular mesh TM, in turn, is formed with relatively inextensible fibers.

Referring again to FIG. 1, robotic device 100 further includes a number of measures of ferrofluid that touches the coils and bladders, and lies within the fluid containment regions. In the present example, the number of measures of ferrofluid include a measure of propulsion ferrofluid 120-1 that touches the propulsion coils PC1-PCn and the propulsion bladder PB, and lies within the propulsion fluid containment region EN.

In the present example, the number of measures of ferrofluid also include a number of measures of steering ferrofluid that corresponds with the number of steering coils. Thus, in the present example, eight measures of steering ferrofluid 120-21, 120-22, 120-23, 120-24, 120-25, 120-26, 120-7, and 120-28 are illustrated.

As shown in FIGS. 2A-2H, each measure of steering ferrofluid touches a corresponding steering coil and steering bladder, and lies within a corresponding steering fluid containment region. In addition, in the present example, each measure of steering ferrofluid is permanently spaced apart from each other and from the measure of propulsion ferrofluid 120-1.

The number of measures of ferrofluid in the present example additionally include a measure of treatment ferrofluid 120-3 that touches the treatment coil TC and treatment bladder TB, and lies within the treatment fluid containment region EC. In the present example, the measure of treatment ferrofluid 120-3 is permanently spaced apart from the measure of propulsion ferrofluid 120-1 and the measures of steering ferrofluid 120-21, 120-22, 120-23, 120-24, 120-25, 120-26, 120-27, and 120-28.

A ferrofluid, which is used to implement the propulsion ferrofluid 120-1, the steering ferrofluids 120-21, 120-22, 120-23, 120-24, 120-25, 120-26, 120-27, and 120-28, and the treatment ferrofluid 120-3, is a mixture of very small (e.g., 10 nm) magnetic particles that are evenly suspended in a fluid, such as water or an organic solvent. The particles, which respond to an externally applied magnetic field, but do not retain magnetization when the magnetic field is removed, are coated to prevent agglomeration. Ferrofluids are commercially available, such as from FeroTec (http://www.ferrotec.com/technology/ferrofluid/.)

Referring again to FIG. 1, in the present example, robotic device 100 also includes an expandable stenting structure 122. As shown in FIG. 1, stenting structure 122 is positioned around treatment bladder TB. Stenting structure 122 is optional, and can be used in conjunction with treatment bladder TB when treatment bladder TB is used to perform balloon angioplasty.

As further shown in FIG. 1, robotic device 100 additionally includes a coil control circuit 124 that is located within central tube 110. Coil control circuit 124, which is connected to the first and second ends of each coil, controls an activation sequence of the propulsion coils PC1-PCn to propel robotic device 100, the activation of one or more of the front and back steering coils SF1-SF4 and SB1-SB4 to steer robotic device 100, and the activation of treatment coil TC to provide balloon angioplasty and stenting.

Figure 4:
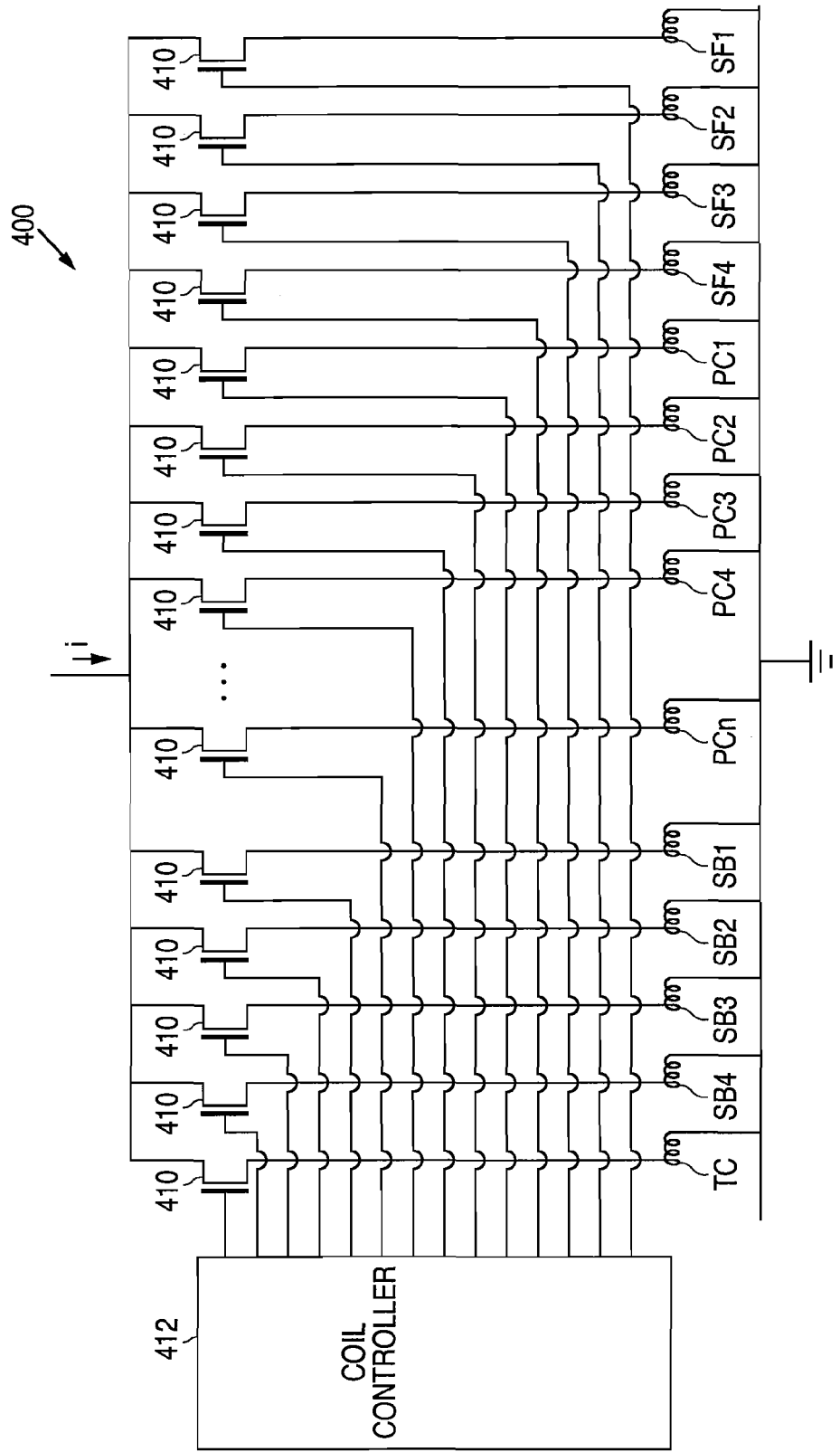
FIG. 4 is a schematic diagram illustrating an example of a coil control circuit 400 in accordance with the present invention.

FIG. 4 shows a schematic diagram that illustrates an example of a coil control circuit 400 in accordance with the present invention. Coil control circuit 400 can be used to implement coil control circuit 124. As shown in FIG. 4, coil control circuit 400 includes a number of switches 410 that are connected to the propulsion coils PC1-PCn, the front steering coils SF1-SF4, the back steering coils SB1-SB4, and the treatment coil TC, and a coil controller 412 that is connected to the switches 410.

In operation, coil controller 412 activates or energizes the propulsion coils PC1-PCn in one or more predefined sequences by adjusting the magnitude of the current that flows through the switches 410 connected to the propulsion coils PC1-PCn. As described in greater detail below, robotic device 100 is propelled by energizing the propulsion coils PC1-PCn in a predefined sequence with a predefined timing.

In addition, coil controller 412 energizes one or more of the front and back steering coils SF1-SF4 and SB1-SB4 as needed to steer robotic device 100 by adjusting the magnitude of the current that flows through the switches 410 to the front and back steering coils SF1-SF4 and SB1-SB4. In the preferred embodiment, steering commands and the selection of a propulsion sequence are received from an external source. Alternately, steering commands and the selection of a propulsion sequence can be derived from sensor data input to coil controller 412. Further, coil controller 412 energizes treatment coil TC as needed to inflate treatment bladder TB as an angioplasty balloon by adjusting the magnitude of the current that flows through the switch 410 to treatment coil TC.

Figure 5A:
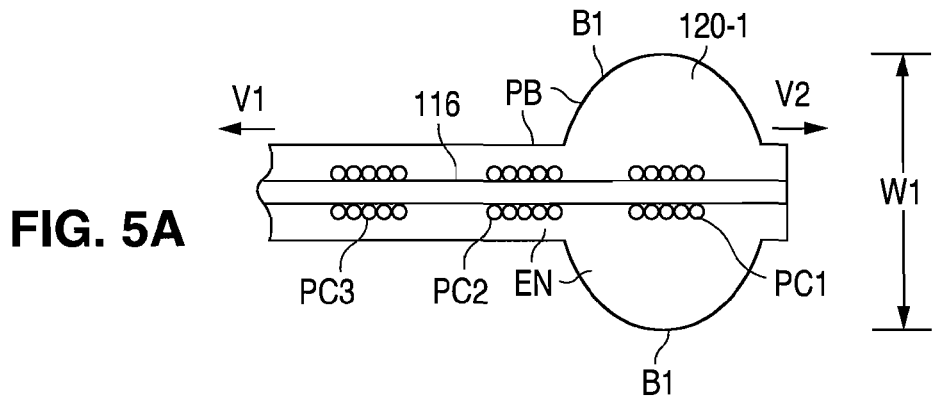
FIGS. 5A-5D are a series of cross-sectional views illustrating a first example of the locomotion of robotic device 100 in accordance with the present invention.

FIGS. 5A-5D show a series of cross-sectional views that illustrate a first example of the locomotion of robotic device 100 in accordance with the present invention. Locomotion begins by passing a current through propulsion coil PC1, which generates a first magnetic field. As shown in FIG. 5A, ferrofluid 120-1 in the propulsion fluid containment region EN is immediately attracted to the first magnetic field which, in turn, causes propulsion bladder PB to immediately bulge out. Thus, ferrofluid 120-1 generates a first bulge B1 that has a maximum width W1 that corresponds with the peak of the magnetic field intensity of the first magnetic field.

As a result, when robotic device 100 is placed in a passageway that includes a material, such as blood, mucus, water, or oil, the immediate bulge in propulsion bladder PB generates a shock wave in the surrounding material. For purposes of simplicity, the shock wave is broken into two force vectors in FIG. 5A: a first vector V1 directed along longitudinal side wall 116, and a second vector V2 that opposes the first vector V1. (The force orthogonal to longitudinal side wall 116 cancels out when bladder PB expands out on opposite sides of central tube 110 at the same time.)

After propulsion bladder PB has reached a fully extended position in response to the activation of propulsion coil PC1, a current is passed through propulsion coil PC2 while maintaining the current flow through propulsion coil PC1. The current flowing through propulsion coil PC2 generates a second magnetic field.

Figure 5B:
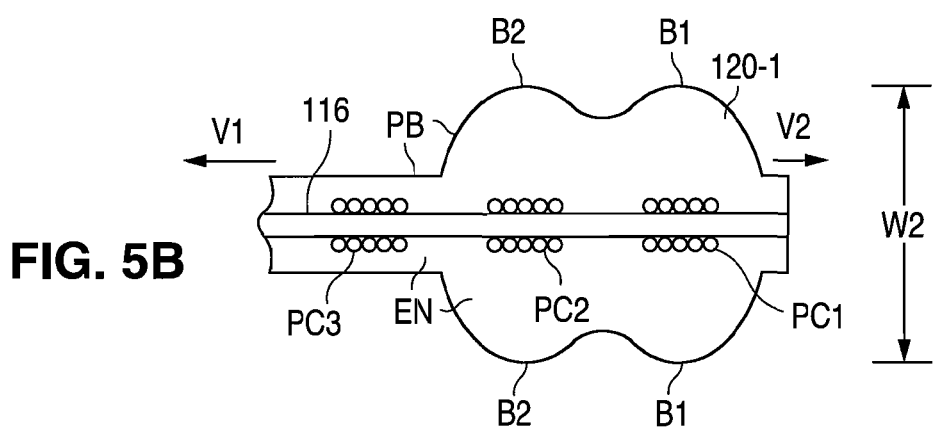

As shown in FIG. 5B, ferrofluid 120-1 in the propulsion fluid containment region EN immediately adjusts to the two magnetic fields by driving out a second bulge B2 in addition to the first bulge B1. The first and second bulges B1 and B2 each have a maximum width W2 that corresponds with the peaks of the magnetic field intensities of the first and second magnetic fields. Because two bulges are now present and the measure of propulsion ferrofluid 120-1 remains the same, the maximum width W2 is less than the maximum width W1.

Driving out second bulge B2, in turn, generates a shock wave that reinforces and substantially increases the first vector V1, while adding little to nothing to the second vector V2. Thus, since the first vector V1 is now substantially larger than the second vector V2, robotic device 100 moves forward (in the opposite direction of the first vector V1).

Figure 5C:
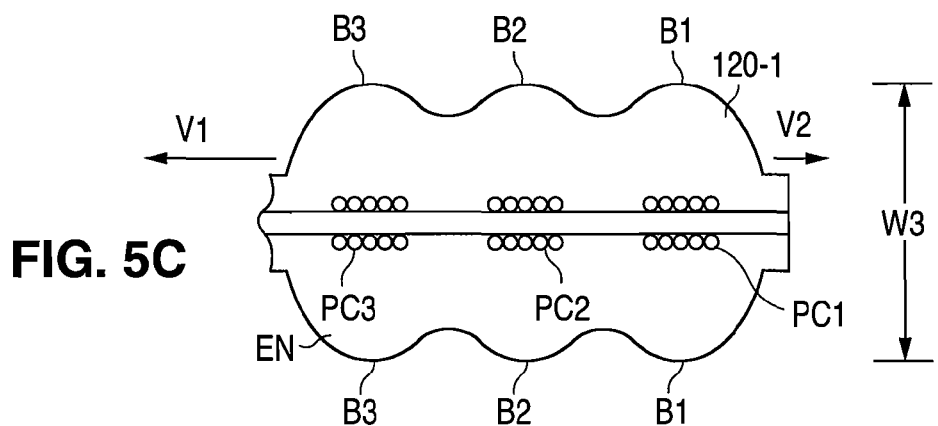

After propulsion bladder PB has reached a fully extended position in response to the activation of propulsion coil PC2, a current is now passed through propulsion coil PC3. The current flowing through propulsion coil PC3 generates a third magnetic field. As shown in FIG. 5C, when the current continues to flow through propulsion coils PC1 and PC2, ferrofluid 120-1 in the propulsion fluid containment region EN immediately adjusts to the three magnetic fields by driving out a third bulge B3 in addition to the first and second bulges B1 and B2.

The first, second, and third bulges B1, B2, and B3 each have a maximum width W3 that corresponds with the peaks of the magnetic field intensities of the first, second, and third magnetic fields. Because three bulges are now present and the measure of propulsion ferrofluid 120-1 remains the same, the maximum width W3 is less than the maximum width W2.

Thus, the maximum width, and thereby the contribution to force vector V1, decreases with each succeeding bulge. As a result, the current through the first propulsion coil PC1 can be stopped when the current through the third propulsion coil PC3 (or a succeeding propulsion coil PC) begins.

Figure 5D:
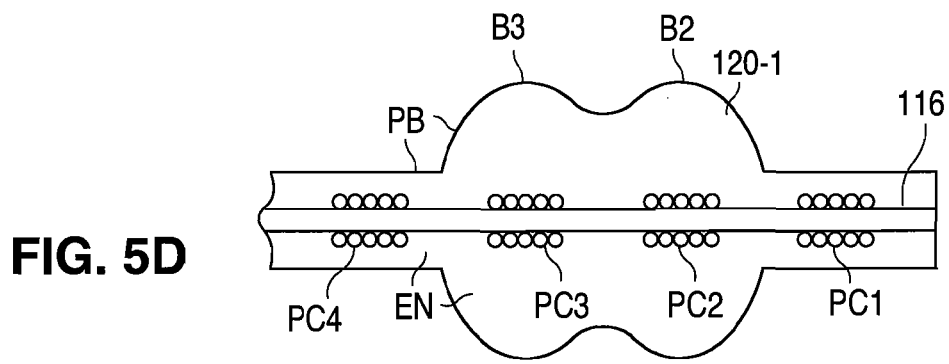

As shown in FIG. 5D, when the current through the first propulsion coil PC1 is stopped as the current through the third propulsion coil PC3 is started, the effect is the formation of two bulges that move down the side of robotic device 100, thereby propelling robotic device 100 forward (in the opposite direction of the first vector V1).

Figure 6A:
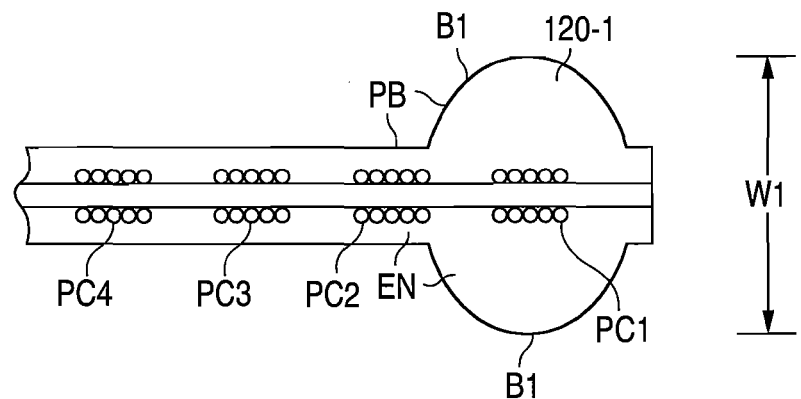
FIGS. 6A-6C are a series of cross-sectional views illustrating a second example of the locomotion of robotic device 100 in accordance with the present invention.
Figure 6B:
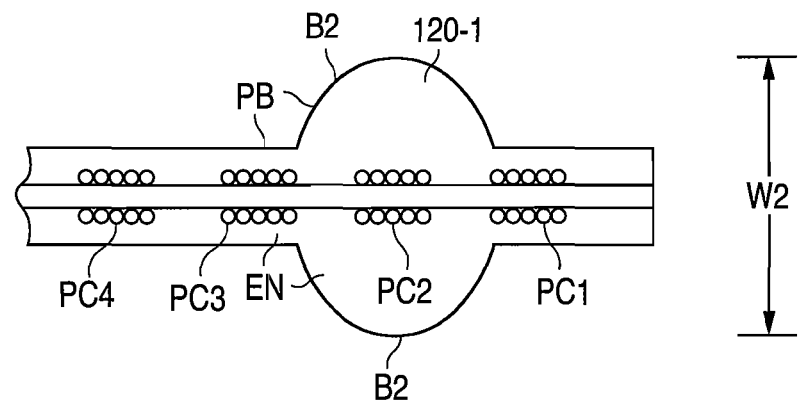
Figure 6C:
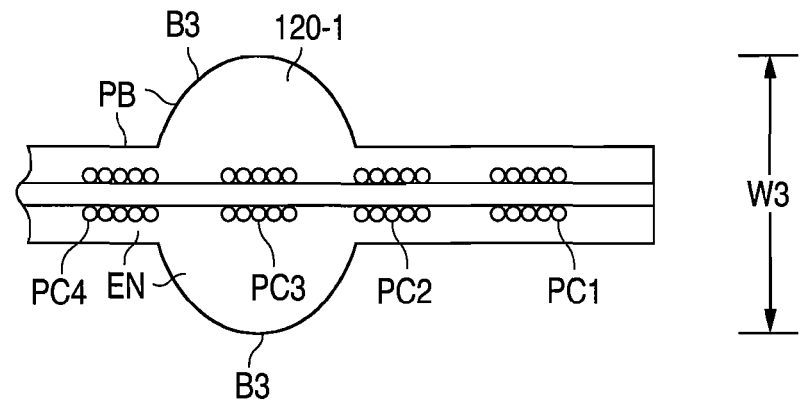

FIGS. 6A-6C show a series of cross-sectional views that illustrate a second example of the locomotion of robotic device 100 in accordance with the present invention. Locomotion begins as in the first example by passing a current through propulsion coil PC1, which generates a first magnetic field.

As shown in FIG. 6A, ferrofluid 120-1 in the propulsion fluid containment region EN is immediately attracted to the first magnetic field which, in turn, causes propulsion bladder PB to immediately bulge out. As above, ferrofluid 120-1 generates a first bulge B1 that has a maximum width W1 that corresponds with the peak of the magnetic field intensity of the first magnetic field.

After propulsion bladder PB has reached a fully extended position in response to the activation of propulsion coil PC1, a current is passed through propulsion coil PC2 while the current flow through propulsion coil PC1 is stopped. The current flowing through propulsion coil PC2 generates a second magnetic field.

As shown in FIG. 6B, ferrofluid 120-1 in the propulsion fluid containment region EN immediately adjusts to the collapse of the first magnetic field and the creation of the second magnetic field by driving out a second bulge B2. The second bulge B2 has a maximum width W2 that corresponds with the peak of the magnetic field intensity of the second magnetic field. Because only one bulge is now present, the maximum width W2 is the same as the maximum width W1.

After propulsion bladder PB has reached a fully extended position in response to the activation of propulsion coil PC2, a current is passed through propulsion coil PC3 while the current flow through propulsion coil PC2 is stopped. The current flowing through propulsion coil PC3 generates a third magnetic field.

As shown in FIG. 6C, ferrofluid 120-1 in propulsion fluid containment region EN immediately adjusts to the collapse of the second magnetic field and the creation of the third magnetic field by driving out a third bulge B3. The third bulge B3 has a maximum width W3 that corresponds with the peak of the magnetic field intensity of the third magnetic field. Because only one bulge is now present, the maximum width W3 is the same as the maximum widths W1 and W2.

Thus, as shown in FIGS. 6A-6C, the formation of a bulge along with the corresponding collapse of the preceding bulge has the effect of forming a single bulge that moves down the side of robotic device 100, thereby propelling robotic device 100 forward (in the opposite direction of the first vector V1 shown in FIGS. 5A-5D).

The propulsion coils PC1-PCn can be energized in other sequences as well. For example, additional switches 410 can be added to coil control circuit 400 so that two propulsion coils PC1-PCn are energized at the same time. In this example, propulsion coils PC1-PC2 are first energized, followed by propulsion coils PC2-PC3, and PC3-PC4 and so on.

In this sequence, the front side of a single larger bulge is continuously collapsed while the back side of the bulge is continuously driven out. This also has the effect of forming a single bulge that moves down the side of robotic device 100, thereby propelling robotic device 100 forward (in the opposite direction of the first vector V1 shown in FIGS. 5A-5D).

Figure 7A:
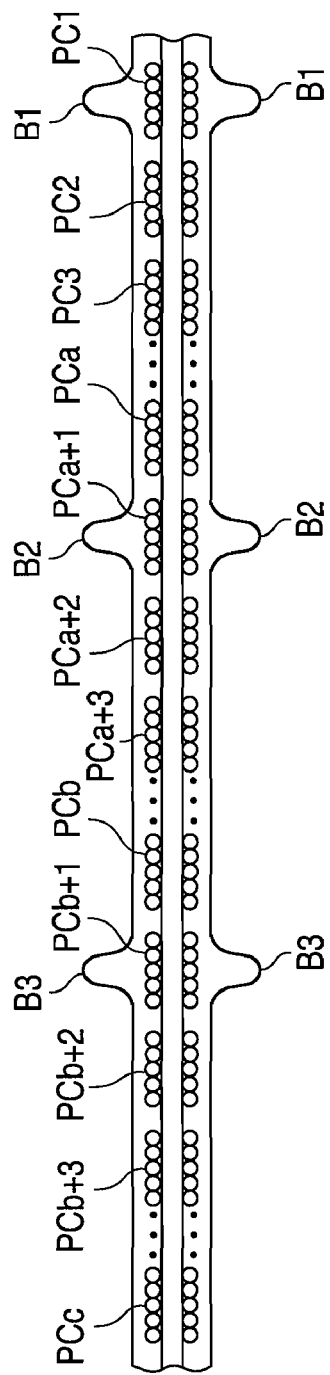
FIGS. 7A-7C are a series of cross-sectional views illustrating a third example of the locomotion of a robotic device 100 in accordance with the present invention.
Figure 7B:
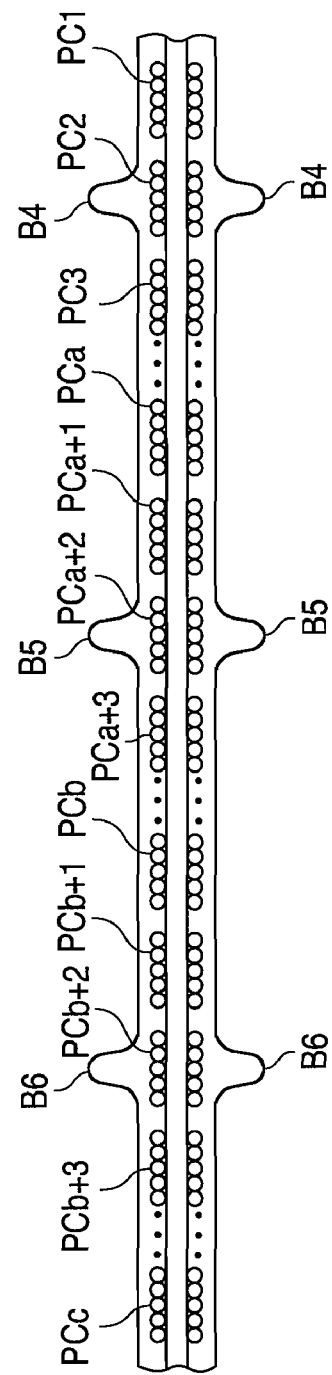
Figure 7C:
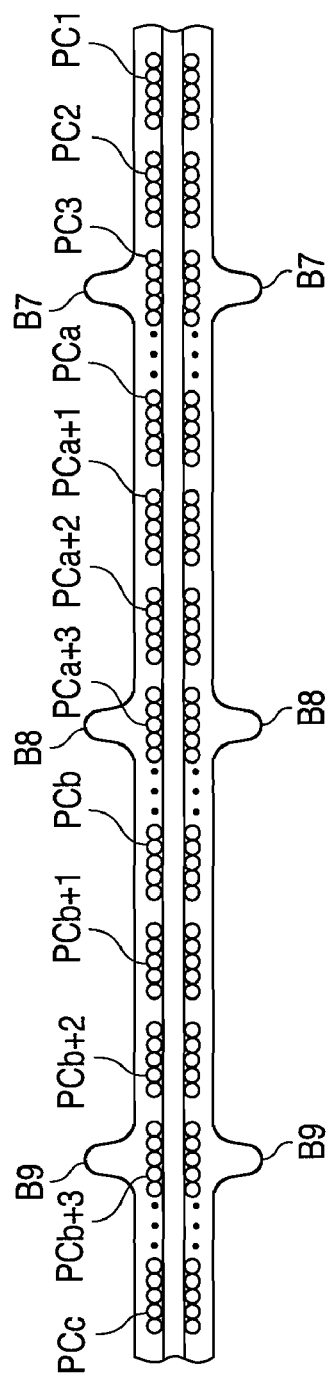

FIGS. 7A-7C show a series of cross-sectional views that illustrate a third example of the locomotion of a robotic device 100 in accordance with the present invention. In this example, the propulsion coils PC1-PCn are separated into a number of groups of propulsion coils, such as a first group having coils $PC_1$-$PC_a$, a second group having $PC_{a+1}$-$PC_b$, and a third group having $PC_{b+1}$-$PC_c$.

As shown in FIG. 7A, locomotion begins by energizing propulsion coils $PC_1$, $PC_{a+1}$, and $PC_{b+1}$ to create bulges B1, B2, and B3. As shown in FIG. 7B, locomotion continues by energizing propulsion coils $PC_2$, $PC_{a+2}$, and $PC_{b+2}$ to create bulges B4, B5, and B6, while de-energizing propulsion coils $PC_1$, $PC_{a+1}$, and $PC_{b+1}$. (Alternately, propulsion coils $PC_1$, $PC_{a+1}$, and $PC_{b+1}$ can remain active as in the FIGS. 5A-5D example.)

As shown in FIG. 7C, locomotion continues by energizing propulsion coils $PC_3$, $PC_{a+3}$, and $PC_{b+3}$ to create bulges B7, B8, and B9, while de-energizing propulsion coils $PC_2$, $PC_{a+2}$, and $PC_{b+2}$. (Alternately, propulsion coils $PC_2$, $PC_{a+2}$, and $PC_{b+2}$ can remain active while propulsion coils $PC_1$, $PC_{a+1}$, and $PC_{b+1}$ are de-energized as in the FIGS. 5A-5D example.)

Thus, as shown in FIGS. 7A-7C, by utilizing a number of groups of coils with a synchronized movement, each group of coils produces a bulge structure that moves down the side of robotic device 100, thereby propelling robotic device 100 forward (in the opposite direction of the first vector V1 shown in FIGS. 5A-5D). Further, the direction of movement of robotic device 100 in each of the examples described above can be reversed by reversing the activation sequence of the propulsion coils PC1-PCn.

FIGS. 8A-8D show a series of cross-sectional views that illustrate a fourth example of the locomotion of a robotic device 100 in accordance with the present invention. In this example, central tube 110 is implemented as an elastic, longitudinally-compressible structure, and the interior side wall of the passageway is semi-rigid to rigid. For example, a blood vessel is semi-rigid whereas a steel pipe is rigid.

Figure 8A:
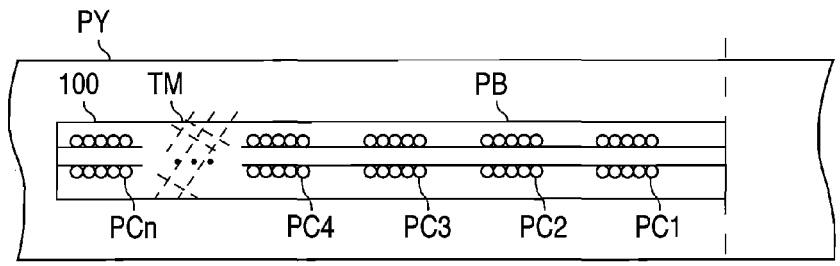
FIGS. 8A-8D are a series of cross-sectional views illustrating a fourth example of the locomotion of a robotic device 100 in accordance with the present invention.

As shown in FIG. 8A, the propulsion coil section of robotic device 100 is illustrated in a passageway PY with all of the propulsion coils PC1-PCn de-energized. As with the first example, locomotion then begins by passing a current through propulsion coil PC1, which generates a first magnetic field.

Figure 8B:
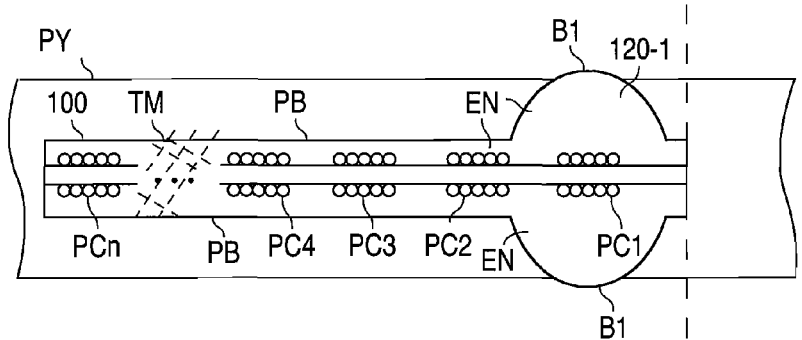

As shown in FIG. 8B, ferrofluid 120-1 in the propulsion fluid containment region EN is immediately attracted to the first magnetic field which, in turn, causes propulsion bladder PB to immediately bulge out and form a first bulge B1 that touches the interior side wall of passageway PY. The current through propulsion coil PC1 is adjusted so that the pressure exerted against the interior side wall of passageway PY is sufficient to lock the first bulge B1 into place.

In addition, the surface area of propulsion bladder PB is kept relatively constant by mesh TM, which responds to the first bulge B1 by decreasing the length of the propulsion coil section of central tube 110. (Mesh TM is shown by dashed lines since mesh TM has only bumps on the exterior surface of bladder PB in cross-section. In addition, only a portion of mesh TM is shown for clarity.) Thus, when propulsion bladder PB bulges out to form first bulge B1, central tube 110 is longitudinally compressed at the same time due to the relatively inextensible fibers of mesh TM.

Figure 8C:
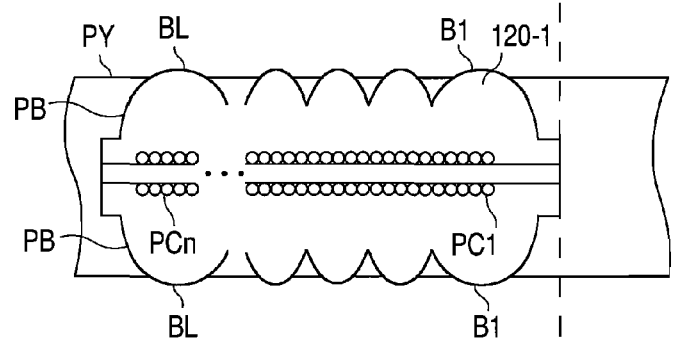
Figure 8D:
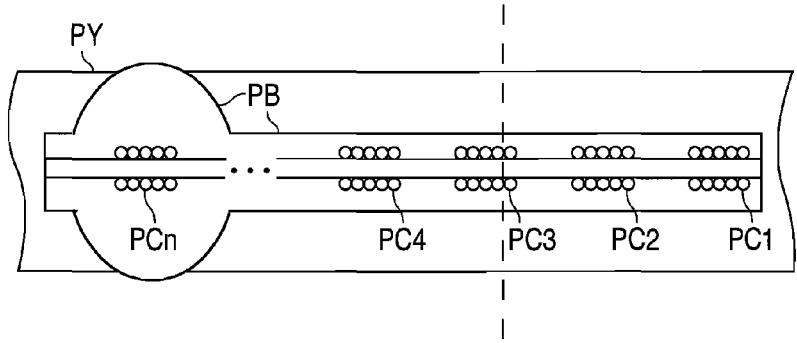

As shown in FIG. 8C, after propulsion bladder PB has reached a fully extended position in response to the activation of propulsion coil PC1, the sequential activation of the remaining propulsion coils PC (while continuing to activate the previous coils) generates corresponding bulges, while at the same time further lengthwise compressing the propulsion section of robotic device 100. When the last propulsion coil PCn has been energized and a last bulge BL has been driven out, the current through propulsion coil PCn is adjusted so that the pressure exerted against the interior side wall of the passageway PY is sufficient to lock the last bulge BL into place. After propulsion bladder PB has reached a fully extended position in response to the activation of propulsion coil PCn, the currents through the previous coils PC1-PCn−1 are now turned off, thereby de-energizing the previous coils and collapsing the magnetic fields associated with the previous coils PC1-PCn−1. As shown in FIG. 8D, since central tube 110 is lengthwise compressed, the deactivation of the previous coils PC1-PCn−1 causes the front end of robotic device 100 to move forward as central tube 110 lengthwise decompresses.

Figure 9A:
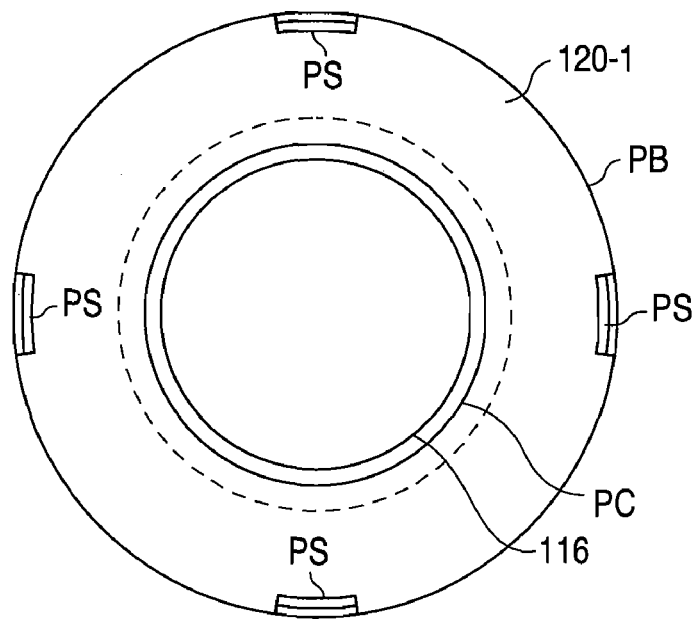
FIGS. 9A-9B are views illustrating an example of the operation of a propulsion coil PC in accordance with the present invention.
Figure 9B:
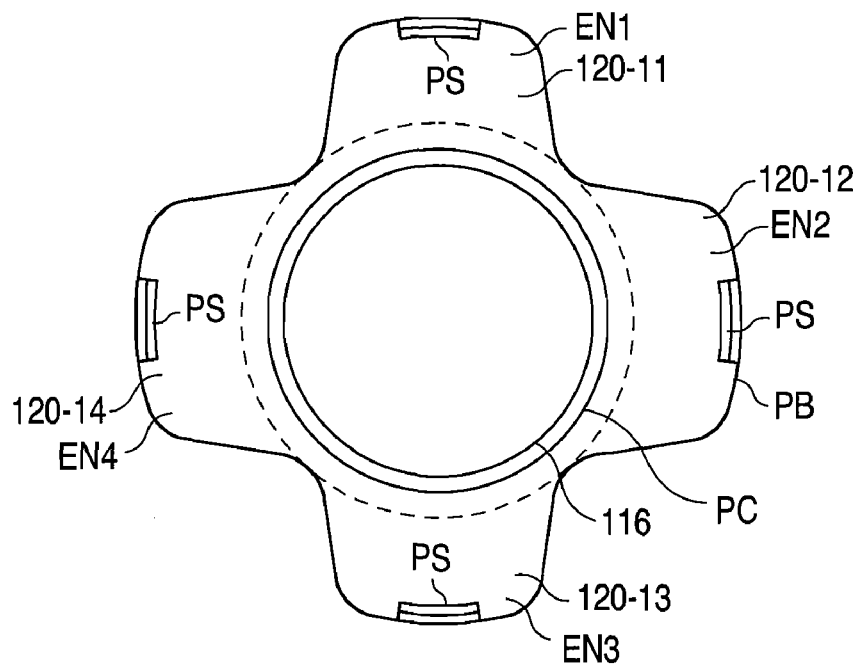

FIGS. 9A-9B show views that illustrate an example of the operation of a propulsion coil PC in accordance with the present invention. FIG. 9A shows a cross-sectional view taken along line 9-9 of FIG. 1 in accordance with a first embodiment, while FIG. 9B shows a cross-sectional view taken along line 9-9 of FIG. 1 in accordance with a second embodiment.

As shown in FIG. 9A, when propulsion coil PC is energized and ferrofluid 120-1 causes the propulsion bladder PB to bulge outwards, the propulsion bladder PB bulges outward an equal amount in all directions. Further, pressure sensors PS can be embedded in propulsion bladder PB to determine if propulsion bladder PB makes contact with the interior wall of a passageway and, if contact is made, to determine the amount of pressure that is applied to the interior wall of the passageway.

Determining the amount of pressure that is applied to the interior wall of the passageway allows the magnitude of the current to be adjusted to control the pressure that is applied to the interior wall of the passageway, or to reduce the magnitude of the current to ensure that propulsion bladder PB does not make contact with the interior wall of the passageway.

Alternately, as shown in FIG. 9B, propulsion bladder PB can be permanently attached to the propulsion coils, including the propulsion coil PC, at four locations to form four propulsion fluid containment regions EN1, EN2, EN3, and EN4 instead of one which, in turn, hold four measures of propulsion ferrofluid 120-11, 120-12, 120-13, and 120-14.

Thus, when propulsion coil PC is energized and ferrofluids 120-11, 120-12, 120-13, and 120-14 causes the propulsion bladder PB to bulge outwards, the propulsion bladder PB bulges outward in four regions. (Other numbers of regions can alternately be used.) Thus, when robotic device 100 moves forward through a passageway where a fluid, such as blood, flows through the passageway, the arrangement shown in FIG. 9B reduces the amount of fluid flow that is blocked by robotic device 100.

In addition to placement on propulsion bladder PB, pressure sensors PS can also be placed on the front and back steering bladders BF and BB. Pressure sensors PS can also be placed on the first and second end caps 114 and 116 as shown in FIG. 1 to detect obstructions. When obstructions are encountered, information from the pressure sensors is transmitted to coil control circuit 124 so that robotic device 100 can back up and move forward in another direction. In addition to pressure sensors, robotic device 100 can optionally include other sensors, such as thermal, electrical, and chemical sensors, depending on the characteristics of the environment which are to be sensed.

Figure 10A:
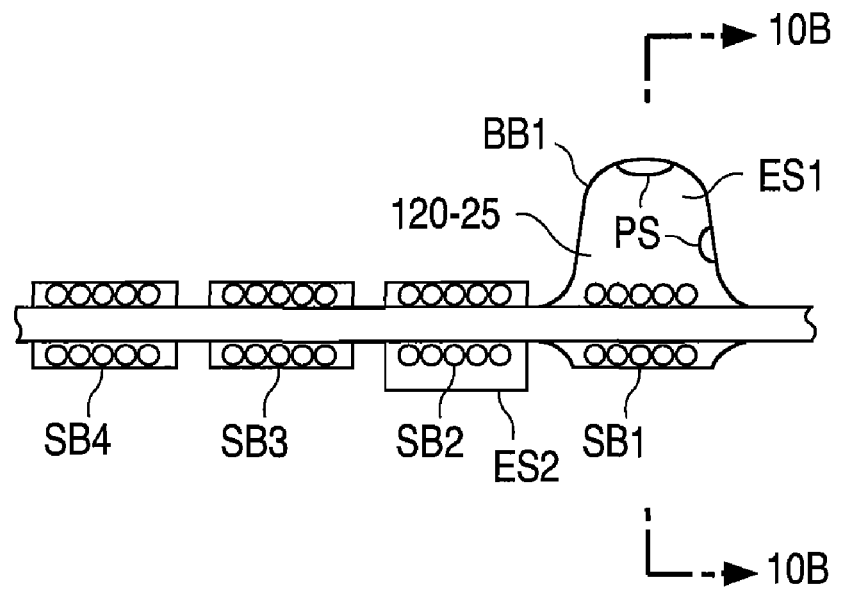
FIGS. 10A-10B are views illustrating a first example of the steering of robotic device 100 in accordance with the present invention.
Figure 10B:
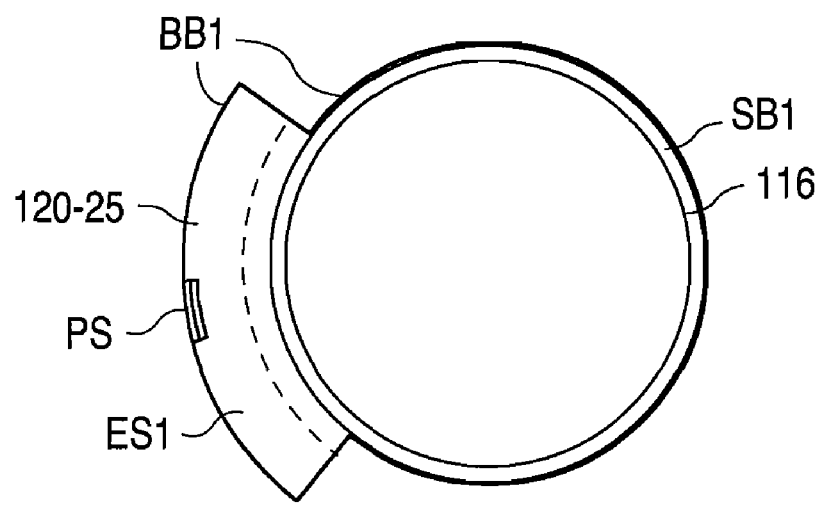

FIGS. 10A-10B show views that illustrate a first example of the steering of robotic device 100 in accordance with the present invention.

FIG. 10A shows a longitudinal cross-sectional view of the back steering coil section of central tube 110, while FIG. 10B shows a cross-sectional view taken along line 10B-10B of FIG. 10A. As shown in FIGS. 10A-10B, forward steering is accomplished by passing currents through one or more of the back steering coils SB.

For example, when a current is passed through steering coil SB1, a magnetic field associated with steering coil SB1 is generated. As shown in FIGS. 10A-10B, ferrofluid 120-25 in the steering fluid containment region ES1 is immediately attracted to the magnetic field which, in turn, causes back steering bladder BB1 to immediately bulge out.

However, unlike propulsion bladder PB in the FIG. 9A example, each steering bladder is permanently attached to a 270° portion of a corresponding steering coil. As a result, only the steering fluid containment region ES that lies above the 90° portion bulges out. Further, the magnitude of the current input into steering coil SB1 can be varied so that the size of the bulge can be varied from a small to a large bulge.

When locomotion is provided as in the first, second, and third examples, the activation of one or more of the back steering coils SB1-SB4 causes the corresponding back bladder BB to bulge out which, in turn, allows robotic device 100 to be steered in a manner somewhat similar to a submarine.

The front steering coils SF1-SF4 operate in the same manner as the back steering coils SB1-SB4, and provide steering when propulsion has been reversed and robotic device 100 is moving backward. In addition, the back and front steering coils SB1-SB4 and SF1-SF4 can be used at the same time to provide precision positioning. Further, robotic device 100 can optionally be implemented with only one set of steering coils (e.g., only the back steering coils SB1-SB4) along with the corresponding bladders.

When locomotion is provided as in the fourth example, where central tube 110 is formed as an elastic, longitudinally-compressible structure, the activation of one or more of the front steering coils SF1-SF4 causes the corresponding bladder BF to bulge out which, in turn, allows robotic device 100 to change direction.

Figure 11A:
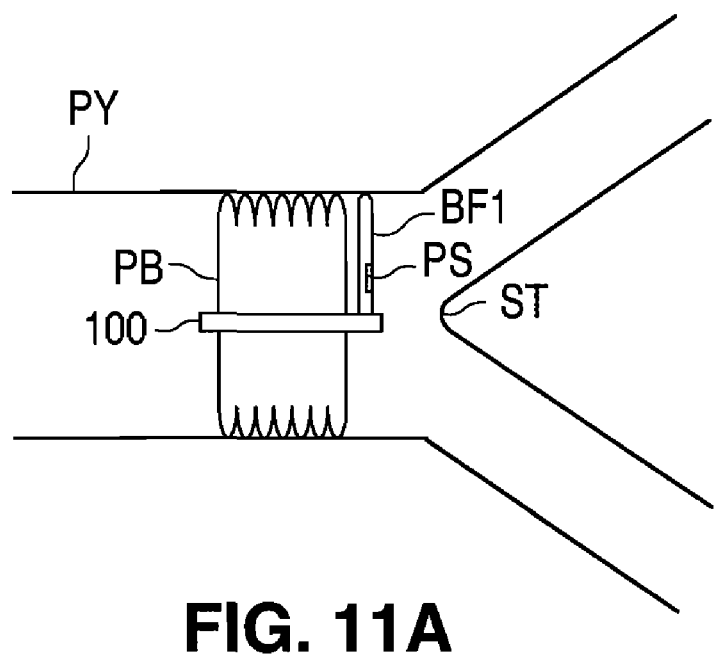
FIGS. 11A-11B are cross-sectional views illustrating a second example of the steering of robotic device 100 in accordance with the present invention.
Figure 11B:
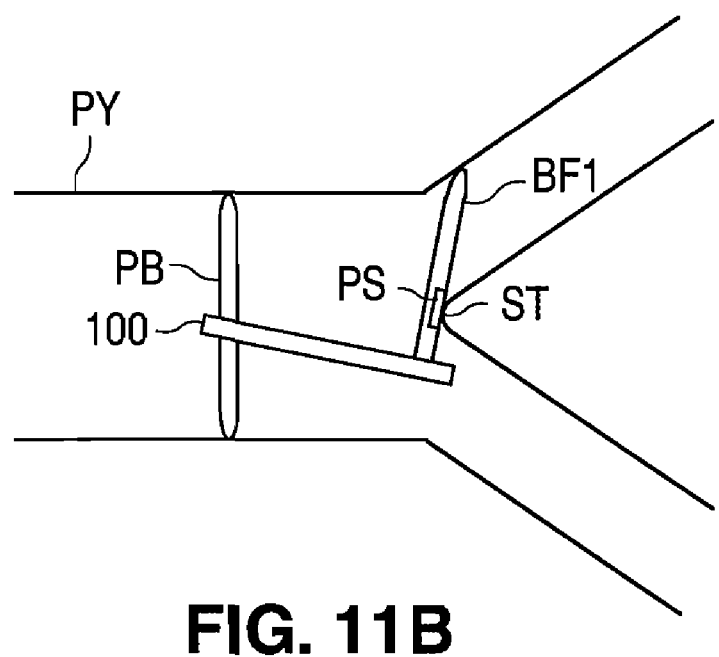

FIGS. 11A-11B show cross-sectional views that illustrate a second example of the steering of robotic device 100 in accordance with the present invention. As illustrated in FIG. 11A, robotic device 100 is shown approaching a split ST in a passageway PY with all of the propulsion coils PC1-PCn and front steering coil SF1 energized. The activation of all of the propulsion coils PC1-PCn causes propulsion bladder PB is bulge out while at the same time fully compressing the propulsion section of robotic device 100. The activation of front steering coil SF1 causes front steering bladder BF1 to also bulge out.

As illustrated in FIG. 11B, by simultaneously increasing the current in front steering coil SF1 (thereby increasing the width of front steering bladder BF1 to be larger than the width of propulsion bladder PB), and de-energizing the propulsion coils PC1-PCn−1, robotic device 100 moves forward as the propulsion section of robotic device 100 lengthwise decompresses, while the increasing width of front steering bladder BF1 guides robotic device past the split into the lower branch of passageway PY.

Further, pressure sensors PS can be placed on the leading sides of the steering bladders so that when, for example, front steering bladder BF1 shown in FIG. 11B makes contact with the split ST, the current through front steering coil SF1 can be reduced, thereby ensuring that robotic device 100 will move into the lower branch of passageway PY.

In addition, to assume a stable position, each of the back steering coils SB1-SB4 and/or front steering coils SF1-SF4 can be simultaneously energized by passing a current through the back steering coils SB1-SB4 and/or front steering coils SB1-SB4 so that the four back steering bladders BB1-BB4 and/or the four front steering bladders BF1-BF4 each bulge out and make contact with the interior wall of the passageway. Pressure sensors PS can be embedded in the steering bladders to monitor the amount of pressure that is applied to the interior wall of the passageway. This allows the magnitude of the current to be adjusted based on the pressure that is applied to the interior wall of the passageway.

Figure 12A:
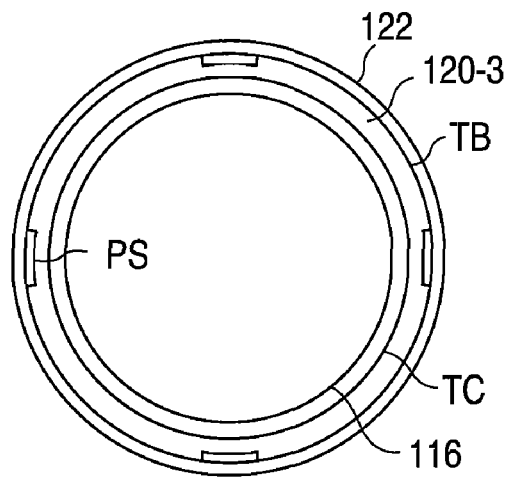
FIGS. 12A-12B are views illustrating an example of the operation of treatment coil TC in accordance with the present invention.
Figure 12B:
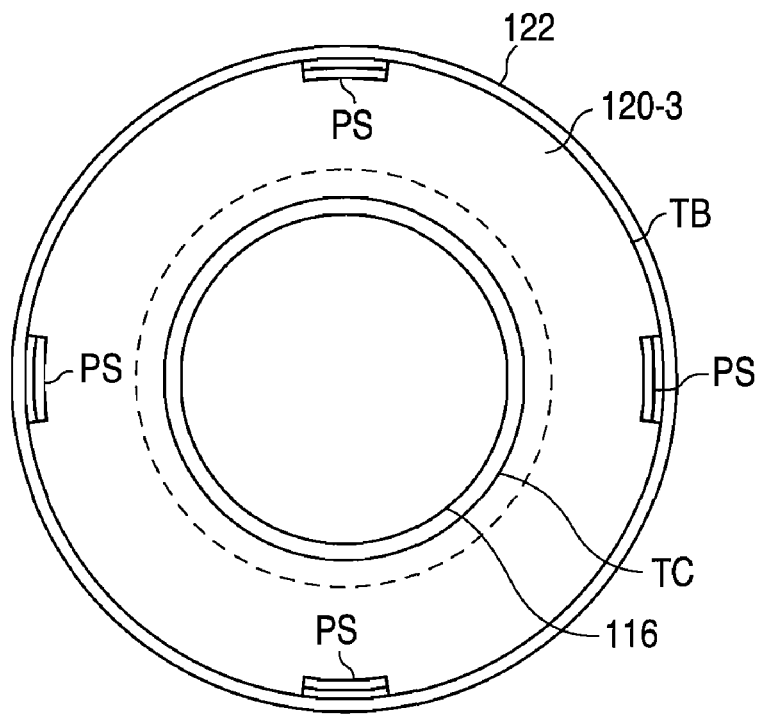

FIGS. 12A-12B show views that illustrate an example of the operation of treatment coil TC in accordance with the present invention. FIG. 12A shows a cross-sectional view taken along line 12-12 of FIG. 1 when treatment coil TC is de-energized, while FIG. 12B shows a cross-sectional view taken along line 12-12 of FIG. 1 when treatment coil TC is energized.

As shown in FIGS. 12A-12B, balloon angioplasty and/or balloon angioplasty and stenting are performed by energizing treatment coil TC by passing a current through treatment coil TC so that treatment bladder TB bulges out and makes contact with the interior wall of the passageway. Further, pressure sensors PS can be embedded in treatment bladder TB to monitor the amount of pressure that is applied to the interior wall of the passageway. This allows the magnitude of the current to be adjusted based on the pressure that is applied to the interior wall of the passageway.

When stenting structure 122 is not present, treatment bladder TB can also be used to obtain a stable position by energizing treatment coil TC by passing a current through treatment coil TC so that treatment bladder TB bulges out and makes contact with the interior wall of the passageway to lock treatment bladder TB to the interior wall of the passageway.

Referring again to FIG. 1, robotic device 100 also includes an imager 128 that is located within central tube 110. Imager 128 generates images of the interior of the passageway from collected image data. The images can be taken to the side, to the front, to the back, or in any combination of directions.

In the present example, imager 128 can be implemented with an imaging circuit 130 that lies within central tube 110, and a number of ultrasound (piezoelectric) transducers 132 that are attached to longitudinal side wall 116 and/or the end caps 112 and 114. The piezoelectric transducers 132 emit sound waves (by converting electrical signals into sound waves) which are reflected off the structures within the passageway.

The reflected sound waves are detected by the piezoelectric transducers 132, which generate imaging data in response to detecting the reflected sound waves. Imaging circuit 130 receives the imaging data and generates an image of the interior of the passageway in response to the imaging data.

Imager 128 can also be implemented with imaging circuit 130, a number of light sources 134, and a number of light detectors 136. The light sources 134 and light detectors 136 are attached to longitudinal side wall 116 and/or the end caps 112 and 114. The light sources 134 emit light, such visible to infrared light, which is reflected off the structures within the passageway.

The reflected light is detected by light detectors 136, such as charge coupled devices (CCD), which generate imaging data in response to detecting the reflected light. Imaging circuit 130 receives the imaging data and generates an image of the interior of the passageway in response to the imaging data. Further, robotic device 100 can utilize both transducers 132 and the sources 134/detectors 136 to generate imaging data.

In addition, robotic device 100 can optionally include one or more instruments 140, such as medical instruments, which can be used to take corrective action on the passageway or structures which can be accessed by way of the passageway. For example, one or more micro-needles can be attached to front end cap 112 to allow the delivery of drugs or other agents. In addition, other instruments, such a forceps and scissors, can be attached to front end cap 112. Further, the ultrasound transducers 132 or additional ultrasound transducers located adjacent to the transducers 132 can be utilized to ablate material attached to the interior of the passageway.

In addition, robotic device 100 can optionally be connected to one or more cables 150. The cables 150 can include, for example, a safety cable for ensuring that robotic device 100 can be withdrawn from the passageway, and electrical cables for transmitting and receiving images, sensor data, power, propulsion and steering commands, treatment commands, imaging commands, and instrumental control commands.

Instead of being connected to electrical cables, robotic device 100 can alternately include a communications circuit 160 that provides wireless transmission of control data from coil control circuit 124, image data from imager 128, instrumental feedback data from instruments 140, sensor data, and other information to an external device, and wireless reception of propulsion commands, steering commands, and treatment commands for coil control circuit 124, imaging commands for imager 128, instrumental control commands for instruments 140, and other information from the external device.

As shown in FIG. 1, communications circuit 160 includes an antenna 162 that receives signals from and transmits signals to the external device. Circuit 160 also includes a transceiver 164 connected to antenna 162 that up converts baseband signals to be output by antenna 162, and down converts signals received from antenna 162 to baseband signals. Further, circuit 160 includes a processor 166 connected to transceiver 164 that outputs the control data, image data, instrumental feedback data, sensor data, and other information to transceiver 164 as baseband signals, and converts a received baseband signal from transceiver 164 into propulsion, steering, and balloon commands which are sent to circuit 124, imaging commands which are sent to circuit 130, instrumental control commands which are sent to instruments 140, and other information. Communications circuit 160 can utilize any frequency that is compatible with the size of antenna 162.

One of the advantages of being attached to no cables or a fewer number of cables is that robotic device 110 can propel itself much faster with less power. If a number of cables 150 are attached to robotic device 100, then robotic device 100 must pull the weight of the cables 150 through the passageway, as well as overcome the drag associated with pulling the cables 150 around corners and bends in the passageway. By reducing or eliminating the number of cables 150 that are attached to robotic device 100, the cable weight and drag can be reduced or eliminated.

In addition, robotic device 100 includes a power supply 170 when power is not provided by way of a cable 150. Power supply 170, which provides power to coil control circuit 124, imager 128, transducers 132, light sources 134, light detectors 136, instruments 140, and communications circuit 160, can be implemented with a battery.

Alternately, power supply 170 can optionally receive power wirelessly from an external source. As shown in FIG. 1, in the wireless option, power supply 170 includes an antenna 172 that receives an AC signal from the external source, a transformer 174 connected to antenna 172 that isolates and passes the AC signal, and a rectifier 176 connected to transformer 174 that generates a DC voltage VDD from the AC signal passed by transformer 174. Power supply 170 can utilize any frequency that is compatible with the size of antenna 172.

When the central tube 110 is implemented as an elastic, longitudinally-compressible structure, the circuit elements of coil control circuit 124, imaging circuit 130, communications circuit 160, and power supply 170 can be implemented in whole or in part as flexible printed circuits or similar structures to accommodate the longitudinal movement.

Thus, a self-propelled robotic device 100 has been described that can move through bodily passageways to provide images and other information regarding the state of the passageways. Further, robotic device 100 can also be used as a platform to provide therapeutic intervention. In addition to bodily passageways, robotic device 100 can move through other passageways, such as pipelines that carry water, oil, or other materials. When used within a human body, all of the outer surfaces of robotic device 100 are biocompatible, or are covered with a conventional biocompatible coating.

It should be understood that the above descriptions are examples of the present invention, and that various alternatives of the invention described herein may be employed in practicing the invention. For example, although robotic device 100 has been described with a number of different external bladders, robotic device 100 can alternately be implemented with a single external bladder.

Figure 13:
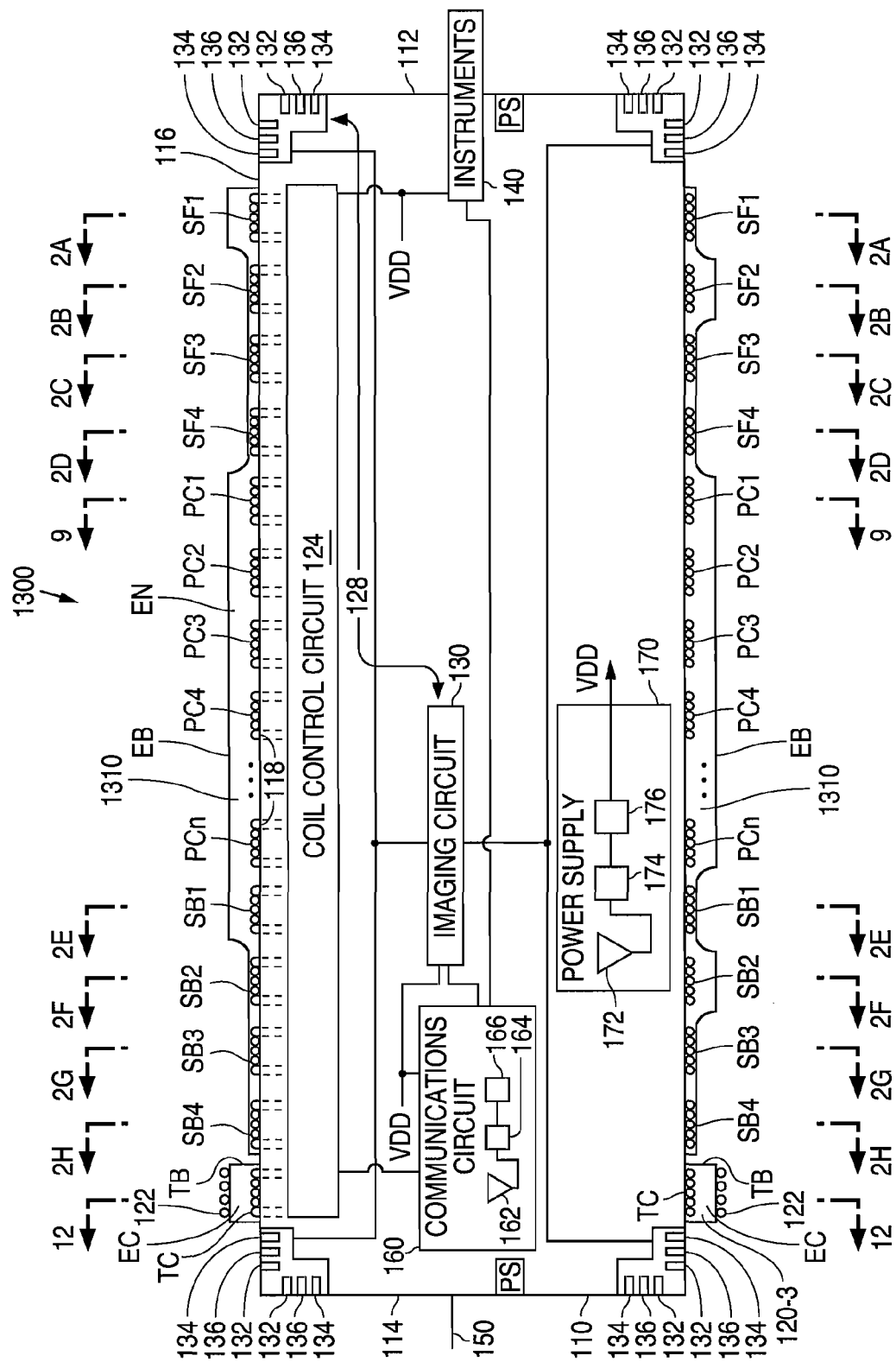
FIG. 13 is a longitudinal cross-sectional view illustrating an example of a robotic device 1300 in accordance with the present invention.

FIG. 13 shows a longitudinal cross-sectional view that illustrates an example of a robotic device 1300 in accordance with the present invention. Robotic device 1300 is similar to robotic device 100 and, as a result, utilizes the same reference numerals to designate the structures which are common to both devices.

As shown in FIG. 13, robotic device 1300 differs from robotic device 100 in that robotic device 1300 utilizes a single external bladder EB in lieu of propulsion bladder PB, the front steering bladders BF1-BF4, and the back steering bladders BB1-BB4, and a single measure of ferrofluid 1310 in lieu of the measures of ferrofluid 120-1, 120-21, 120-22, 120-23, 120-24, 120-25, 120-26, 120-27, 120-28, and 120-3.

Figure 14:
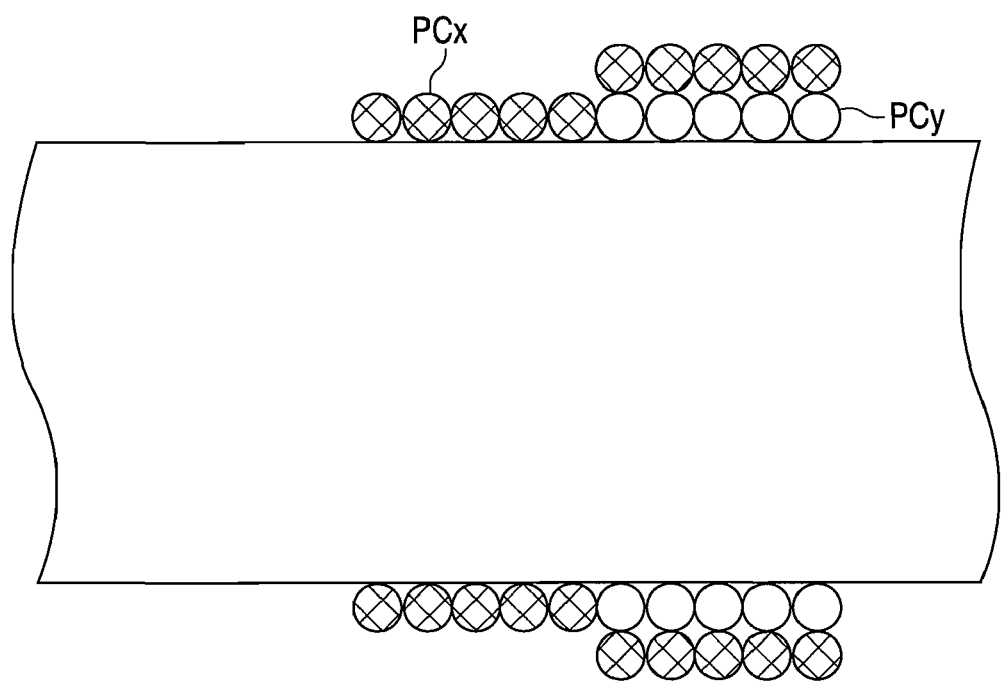
FIG. 14 is a cross-sectional view illustrating an example of a pair of adjacent propulsion coils in accordance with the present invention.

Further, although the present invention has been illustrated with spaced apart coils, one or more of the coils can touch an adjacent coil and form an overlying wrap layer. FIG. 14 shows a cross-sectional view that illustrates an example a pair of adjacent coils in accordance with the present invention.

As shown in FIG. 14, a portion of a second coil PCx (shown hatched) can touch and overlie a portion of an adjacent first coil PCy. By using the wire from second coil PCx to form a second layer of wraps over first coil PCy, the shape of the magnetic field can be adjusted which, in turn, adjusts the shape of the overlying bladder when the coils are energized.

Therefore, it is intended that the following claims define the scope of the invention and that structures and methods within the scope of these claims and their equivalents be covered thereby.

What is claimed is:

1. A robotic device comprising:
   a central tube having a length;
   a plurality of wires wrapped around the central tube to form a plurality of propulsion coils;
   a propulsion bladder attached to the central tube to cover the plurality of propulsion coils;
   wherein the propulsion bladder is expandable away from each propulsion coil by an equal amount in all directions that are orthogonal to the length of the central tube;
   also wherein the propulsion bladder is expandable away from each propulsion coil by different amounts in different directions that are orthogonal to the length of the central tube;
   a measure of propulsion ferrofluid that touches the plurality of propulsion coils and the propulsion bladder;
   a coil control circuit connected to the plurality of propulsion coils, the coil control circuit being positioned within the central tube, and spaced apart from the measure of propulsion ferrofluid, the coil control circuit to control current flow through the plurality of propulsion coils;
   a plurality of wires wrapped around the central tube to form a plurality of steering coils;
   a plurality of steering bladders attached to the central tube to cover the plurality of steering coils so that each steering bladder covers a corresponding steering coil, each steering bladder being expandable away from a steering coil in a direction that is orthogonal to the length of the central tube, a portion of each steering bladder being permanently attached to a corresponding steering coil; and
   a plurality of measures of steering ferrofluid, each measure of steering ferrofluid to touch a corresponding steering coil and a corresponding steering bladder.

2. The robotic device of claim 1 wherein the coil control circuit is connected to the plurality of steering coils.

3. The robotic device of claim 2 and further comprising:
   a wire wrapped around the central tube to form a treatment coil, the treatment coil being spaced apart from the plurality of propulsion coils and the plurality of steering coils; and
   a treatment bladder attached to the central tube to cover the treatment coil in a direction that is orthogonal to the length of the central tube.

4. The robotic device of claim 3 and further comprising a measure of treatment ferrofluid that touches the treatment coil and the treatment bladder, the measure of treatment ferrofluid being permanently spaced apart from the measure of propulsion ferrofluid and the plurality of measures of steering ferrofluid.

5. The robotic device of claim 4 and further comprising a plurality of pressure sensors attached to the propulsion bladder, the plurality of steering bladders, and the treatment bladder, and connected to the coil control circuit, the coil control circuit to alter a magnitude of a current that flows into a coil in response to a signal from a pressure sensor.

6. The robotic device of claim 1 and further comprising an imager attached to the central tube, the imager to generate images of an interior of a passageway.

7. The robotic device of claim 6 wherein the imager includes:
   a plurality of ultrasound transducers attached to the central tube, the plurality of ultrasound transducers to output sound waves, detect reflected sound waves, and output imaging data in response to detecting reflected sound waves; and
   an imaging circuit connected to the plurality of ultrasound transducers, the imaging circuit to lie within the central tube, receive the imaging data, and generate an image of the interior of the passageway in response to the imaging data.

8. The robotic device of claim 6 wherein the imager includes:
   a light source attached to the central tube, the light source to emit light;
   a light detector attached to the central tube, the light detector to detect reflected light, and output imaging data in response to detecting reflected light; and
   an imaging circuit connected to the light detector, the imaging circuit to lie within the central tube, receive the imaging data, and generate an image of the interior of the passageway in response to the imaging data.

9. The robotic device of claim 6 and further comprising a communication circuit that lies within the central tube, the communication circuit to be connected to the coil control circuit and the imager, transmit control data generated by the coil control circuit and images generated by the imager to an external device, and transmit coil control commands received from the external device to the coil control circuit, and image control commands received from the external device to the imager.

10. The robotic device of claim 9 wherein the communication circuit includes an antenna to transmit and receive signals, a transceiver to up convert basebands signals to be output to the antenna and down convert signals received from the antenna to baseband signals, and a processor to generate baseband signals to be output to the transceiver and receive baseband signals from the transceiver.

11. The robotic device of claim 9 and further comprising a power supply that lies within the central tube, the power supply to provide a supply voltage to the coil control circuit, the imager, and the communication circuit.

12. The robotic device of claim 11 wherein the power supply includes an antenna to receive an AC signal, a transformer connected to the antenna to isolate and pass the AC signal, and a rectifier connected to the transformer to generate the supply voltage in response to the AC signal passed by the transformer.

13. The robotic device of claim 11 and further comprising an instrument attached to the central tube, the instrument to receive the supply voltage from the power supply, receive instrument commands from the communication circuit, and transmit instrument data to the communication circuit.

14. The robotic device of claim 13 wherein the instrument includes a plurality of ultrasound transducers attached to the central tube, the plurality of ultrasound transducers to output sound waves to ablate a material attached to an interior side wall of a passageway.

* * * * *